(12) United States Patent
Bain et al.

(10) Patent No.: US 8,449,777 B2
(45) Date of Patent: May 28, 2013

(54) OXIDATION PROCESS

(75) Inventors: Thomas W. Bain, Mississauga (CA); Graham Edward Swales, Orillia (CA)

(73) Assignee: Great Lakes Clean Water Limited Partnership, Mississauga (CA)

( * ) Notice: Subject to any disclaimer, the term of this patent is extended or adjusted under 35 U.S.C. 154(b) by 284 days.

(21) Appl. No.: 12/219,186

(22) Filed: Jul. 17, 2008

(65) Prior Publication Data
US 2009/0026147 A1 Jan. 29, 2009

Related U.S. Application Data (60) Provisional application No. 60/935,128, filed on Jul. 26, 2007.

(51) Int. Cl.
*C02F 1/78* (2006.01)

(52) U.S. Cl.
USPC ........... 210/746; 210/760; 210/764; 210/766; 210/192; 210/205

(58) Field of Classification Search
USPC .................. 210/750, 760, 765, 721, 746, 192, 210/204, 137, 96.1, 167.3, 198.1, 808, 764, 210/766, 20, 5; 261/DIG. 42; 422/28, 33
See application file for complete search history.

(56) References Cited

U.S. PATENT DOCUMENTS

| | | | | |
|---|---|---|---|---|
| 2,606,150 A | * | 8/1952 | Thorp | 210/760 |
| 3,674,216 A | * | 7/1972 | Blair | 241/18 |
| 4,255,257 A | * | 3/1981 | Greiner et al. | 210/760 |
| 4,555,335 A | * | 11/1985 | Burris | 210/192 |
| 4,661,264 A | | 4/1987 | Goudy, Jr. | |
| 4,689,154 A | * | 8/1987 | Zimberg | 210/667 |
| 4,816,145 A | | 3/1989 | Goudy, Jr. | |
| 5,043,079 A | | 8/1991 | Hallett | |
| 5,075,016 A | | 12/1991 | Barnes | |
| 5,160,606 A | | 11/1992 | De Simone et al. | |
| 5,186,841 A | * | 2/1993 | Schick | 210/760 |

(Continued)

OTHER PUBLICATIONS

"Flash Reactor," Mazzei Injector Company website, accessed Jul. 2009 (http://www.mazzei.net/products/flash_reactor.htm).*

(Continued)

*Primary Examiner* — Lucas Stelling
(74) *Attorney, Agent, or Firm* — Bereskin & Parr LLP; Kenneth Bousfield; Philip Mendes da Costa (57) ABSTRACT

A batch process for the treatment of an aqueous solution so that the treated product is more desirable for disposal includes obtaining an influent batch of aqueous solution for treatment, treating the batch of solution by an advanced oxidation process. The advanced oxidation process including causing ozone to be mixed with the solution, maintaining the mixture of solution and ozone at a pressure above atmospheric for a time of at least two seconds. In a preferred embodiment of the process, the process includes continuously recirculating the fluid to be treated, through a recirculation conduit, the recirculation conduit including an ozone injector and the ozone injector is adapted to inject ozone into the aqueous solution as the aqueous solution circulates through an ozone injector. Influent to be treated may be selected from the group including sewage, septage, leachate, ballast or other aqueous solutions where it is desirable to treat the fluid prior to disposal, further treatment, or reuse. The process is carried out to improve a level of disinfection and/or denutrification of the effluent.

40 Claims, 4 Drawing Sheets

U.S. PATENT DOCUMENTS

| | | | |
|---|---|---|---|
| 5,302,288 | A | 4/1994 | Meidl et al. |
| 5,348,664 | A * | 9/1994 | Kim et al. .................... 210/746 |
| 5,409,616 | A | 4/1995 | Garbutt et al. |
| 5,427,693 | A | 6/1995 | Mausgrover et al. |
| 5,493,743 | A | 2/1996 | Schneider et al. |
| 5,498,330 | A | 3/1996 | Delle Cave |
| 5,683,576 | A | 11/1997 | Olsen |
| 5,851,407 | A | 12/1998 | Bowman et al. |
| 6,013,189 | A | 1/2000 | Burris |
| 6,024,882 | A | 2/2000 | McNeilly et al. |
| 6,039,884 | A | 3/2000 | Burris et al. |
| 6,068,778 | A | 5/2000 | Steiner et al. |
| 6,146,524 | A | 11/2000 | Story |
| 6,153,111 | A | 11/2000 | Conrad et al. |
| 6,235,207 | B1 | 5/2001 | Conrad |
| 6,402,945 | B1 | 6/2002 | Swales et al. |
| 6,669,838 | B1 | 12/2003 | Baarman |
| 6,673,251 | B2 * | 1/2004 | Swales et al. ................ 210/760 |
| 6,730,214 | B2 * | 5/2004 | Mazzei ........................ 210/750 |
| 6,783,679 | B1 | 8/2004 | Rozich |
| 6,821,443 | B2 * | 11/2004 | Kim ............................. 210/760 |
| 7,264,419 | B2 | 9/2007 | Bowman et al. |
| 2005/0145575 | A1 * | 7/2005 | Yasunaga et al. ............ 210/760 |
| 2009/0050572 | A1 | 2/2009 | McGuire et al. |
| 2009/0230059 | A1 | 9/2009 | McGuire et al. |

OTHER PUBLICATIONS

"Flash Reactor Peformance," Mazzei Injector Company website, accessed Jul. 2009 (http://www.mazzei.net/products/flash_reactor_performance.html).*

"Pipeline Flash Reactor" Mazzei Injector Company website, accessed Jul. 2009 (http://www.mazzei.net/products/pipeline_flash_reactor.html).*

Google search results for "mazzei FR-75-X", accessed Jul. 2009.*

Undated paper entitled "Inactivation of *Giardia* and *Cryptosporidium* Using Ozone" by G.R. Finch and E.K. Black, Environmental Engineering and Science Program, Department of Civil Engineering, University of Alberta, Edmonton, Alberta Canada T6G 2G7.

Undated paper entitled "Inactivation of *Giardia muris* Using Ozone and Ozone-Hydrogen Peroxide" by C.W. Labatiuk and G.R. Finch, Environmental Engineering and Science Program, Department of Civil Engineering, University of Alberta, Edmonton, Alberta, Canada T6G 2G7.

Article entitled "Comparison of *Giardia lamblia* and *Giardia muris* Cyst Inactivation by Ozone" by G.R. Finch, E.K. Black, C.W. Labatiuk, L. Gyurek and M. Belosevic, University of Alberta, published Applied and Environmental Microbiology, Nov. 1993, p. 3674-3680, American Society for Microbiology.

Undated paper entitled "Summary of research documents on *Cryptosporidium* abstracted between 1995 and 1998" from Department of the Environment Transport and the Regions, 2004.

Undated paper entitled "Reaction of Commonly Used Chemicals with Ozone".

Undated paper entitled "Ozone Mass Transfer Analysis of an Injector with a Flash-Mix Reactor", by A.Bale, M. Gamal El-Din, D.W. Smith all of University of Alberta, A. Moawad of University of Cairo, P. Overbeck of GDT Water Process Corporation, Phoenix, Arizona and A. Mazzei of Mazzei Injector Corporation of Bakersfield, California.

Paper entitled "A Comparison of Point-of-Use Disinfection Methods" by P. Regunathan, PhD and W.H. Beauman, dated 2008.

* cited by examiner

OXIDATION PROCESS

This application claims benefit from U.S. provisional application Ser. No. 60/935,128 filed Jul. 26, 2007, which is incorporated herein by reference in its entirety. In addition a system and apparatus are described in our previous U.S. Pat. No. 6,402,945 and U.S. Pat. No. 6,673,251, the entire disclosures of which are incorporated herein by reference.

FIELD OF THE INVENTION

This invention relates to a method and apparatus for the treatment of water. In particular, the method and apparatus may be used to treat aqueous solutions to make those aqueous solutions more desirable or fit for disposal, either back to the environment or to render such aqueous solutions more fit for further treatment in other treatment facilities.

BACKGROUND OF THE INVENTION

In the field of water treatment, great efforts have been made to deal with disinfection of water. Aqueous solutions requiring treatment include fluids some times referred to as grey water, that is, water which may be produced domestically, containing soap, washing fluids, and the like. Treatment is also required of black water, which is commonly referred to as sewage. There is no real difference between the biological and chemical profiles of grey water and black water. There is no real separation between grey water and black water and in most household situations, all such water is treated as though it were sewage. Sewage is often treated by central, municipally operated treatment plants. However, sewage is often also treated in local facilities, some times referred to as septic tanks. There are a number of options for local treatment competitive with septic tank treatment technology including various forms of bio-digesters and the like.

There are many other fluids which are not suitable for general disposal back to the atmosphere. Some examples in addition to grey/black water, domestic or industrial sewage include septage, leachate, pharmaceutical waste streams and ship ballast fluids.

In the case of septic tanks or similar systems, a processing tank (reactor) is normally provided. In order to keep the septic tank system working for its normal useful life, the septic tank is intended to be pumped periodically to remove the solids and heavy liquids which collect in the bottom of the septic tank. This pumped out material is often referred to as septage. In some jurisdictions, septage can be distributed over agricultural land provided that the septage is widely distributed so as to have an acceptable local effect so that natural digestion of the material is safely accomplished. However, a number of jurisdictions are either banning outright or severely restricting the amount of septage that can be spread on the ground. Where such regulations exist, then septage must be treated in a municipal operated sewage treatment system or some such similar facility. Septage is, in large measure, a concentrated collection of materials precipitated in the septic tank and may require significant dilution before being acceptable to the operator of the treatment facility. Accordingly, it would be advantageous to be able to treat septage so as to make the septage more readily acceptable to the operators of sewage treatment plants.

Rain or ground water passing through a waste dump site, can leach various compounds from the dump. The water collected at the bottom of a dump site is some times referred to as leachate. Leachate can be a significant source of what is termed "pollution", that is, material being released to the environment which is not acceptable in the environment.

It would be desirable to have a system for treating leachate, which is an aqueous solution, to make the leachate more suitable for either release to the environment or for further treatment in other treatment facilities.

It is becoming recognized, that treated water flowing from some treatment plants is a source which releases pharmaceuticals into the environment. When mammals are prescribed pharmaceuticals, the pharmaceuticals are introduced into the body and utilized by the body. However, in most cases, the pharmaceutical is not completely metabolized in the body. Thus, at least some of the pharmaceuticals injested may be excreted from the body. Also, many pharmaceuticals are designed to be stable (non-reactive) in a bacterial environment (namely the human gut) and are not broken down in bioreactors. In other cases, some of the medicine may be metabolized to secondary compounds, but not utilized by the body, and these also are excreted, and then become a component in sewage. Often these pharmaceuticals, whether as primary products or as secondary products, are not effectively treated in some sewage treatment plants. This results in pharmaceuticals being released into the environment.

Cargo ships and other large vessels often take on or discharge ballast water to control ship operating parameters. Discharge of untreated ballast water may involve release of invasive pathogens and species into non-native environments. Thus, there is a need to treat ballast water prior to release to inhibit these problems.

Thus, there are many sources of aqueous solutions that could benefit by treatment. In some cases the treatment may be satisfactory to give treated aqueous solution acceptable for disposal, while in other cases the treatment may render the aqueous solution a more acceptable product for further treatment in other facilities.

U.S. Pat. No. 6,402,945 and U.S. Pat. No. 6,673,251 illustrate an apparatus and system for treating aqueous solutions by injecting ozone into a recirculation conduit. While those patents illustrate useful methods and apparatus, it would be advantageous to have a process and system which not only disinfects, but also has other beneficial affects on the treatment of the aqueous solution.

Among other of the components of sewage are typically phosphorus and nitrogen. Where there are a concentration of septic systems such as in rural homes or cottages surrounding a lake or river, there may eventually be an overload of phosphorus and nitrogen compounds released by the septic systems into the ground water and ultimately, the lake or river. As development around a localized water resource occurs, there will ultimately become a point at which the natural environment will not be able to safely handle the amount of phosphorus and nitrogen released from the septic systems. When the presence of these nutrients increases, certain plant species such as algae or phytoplankton can grow above normal levels which in turn causes problems for the other species trying to grow around them. Excessive algae growth blocks sunlight from the vegetation beneath the water's surface which can cause massive die off of plant species. It also produces a significant amount of organic material that also uses up valuable oxygen as it decomposes and contributes to foul smelling and tasting water.

SUMMARY OF THE INVENTION

In accordance with the invention, an apparatus for treating aqueous solutions for disposal, comprises a processing tank (reactor), the processing tank (reactor) having a fluid inlet and a fluid outlet. The apparatus also includes a recirculation conduit, the recirculation conduit being fluidly connected to the fluid inlet and the fluid outlet. The recirculation conduit includes a pump for recirculating fluid in the processing tank (reactor) through the conduit and back into the processing tank (reactor) in a flow direction. The recirculation conduit also includes an ozone injector for injecting ozone into fluid being circulated by the pump. The ozone injector is downstream of the pump. The recirculation conduit also includes a pressure valve. The pressure valve is located within the recirculation conduit downstream of the ozone injector. The pressure valve is adapted to maintain a pressure in the portion of the recirculation conduit between the pump and the valve at a pressure above atmospheric.

A process in accordance with the invention for the treatment of aqueous solutions so that the treated product is more desirable for disposal, includes obtaining an aqueous solution for treatment. The aqueous solution is treated by an advanced oxidation process. The advanced oxidation process includes causing ozone to be mixed with the influent. The process further includes maintaining the mixture of influent and ozone at a pressure above atmospheric for a time of at least two seconds.

A system in accordance with the invention includes measuring the oxidation/reduction potential (ORP) of the solution being treated and continuing the treatment process until the ORP reaches a predetermined level.

BRIEF DESCRIPTION OF THE DRAWINGS

Further and other features of the invention will be more clearly understood from discussion of the following examples of processes and apparatus in accordance with various embodiments in accordance with the invention. Drawings illustrating an apparatus in accordance with embodiments of the invention follow and, in which.

DETAILED DESCRIPTION OF THE INVENTION

The basic mechanism for treating an aqueous solution to render it more desirable for disposal in accordance with this invention involves an advanced oxidation process. In an advanced oxidation process, the aqueous solution is mixed with ozone. When ozone is mixed with an aqueous solution, the ozone inter-reacts with the compounds and organisms within the solution to reduce the amount of undesired chemicals in, and disinfection of the solution. Such a system and apparatus are described in our previous U.S. Pat. No. 6,402,945 and U.S. Pat. No. 6,673,251, the entire disclosures of which are incorporated herein by reference.

It has surprisingly been found that there are very substantial benefits that may be obtained by maintaining a mixture of the aqueous solution and ozone under pressure above atmospheric for at least a selected time period. We have shown that increasing the pressure to which the mixture is subjected provides increased results. We have also shown that increasing the time under which the mixture is kept at increased pressure also has desirable benefits in the treatment of the aqueous solution, thereby rendering it more desirable for disposal.

Figure 1:
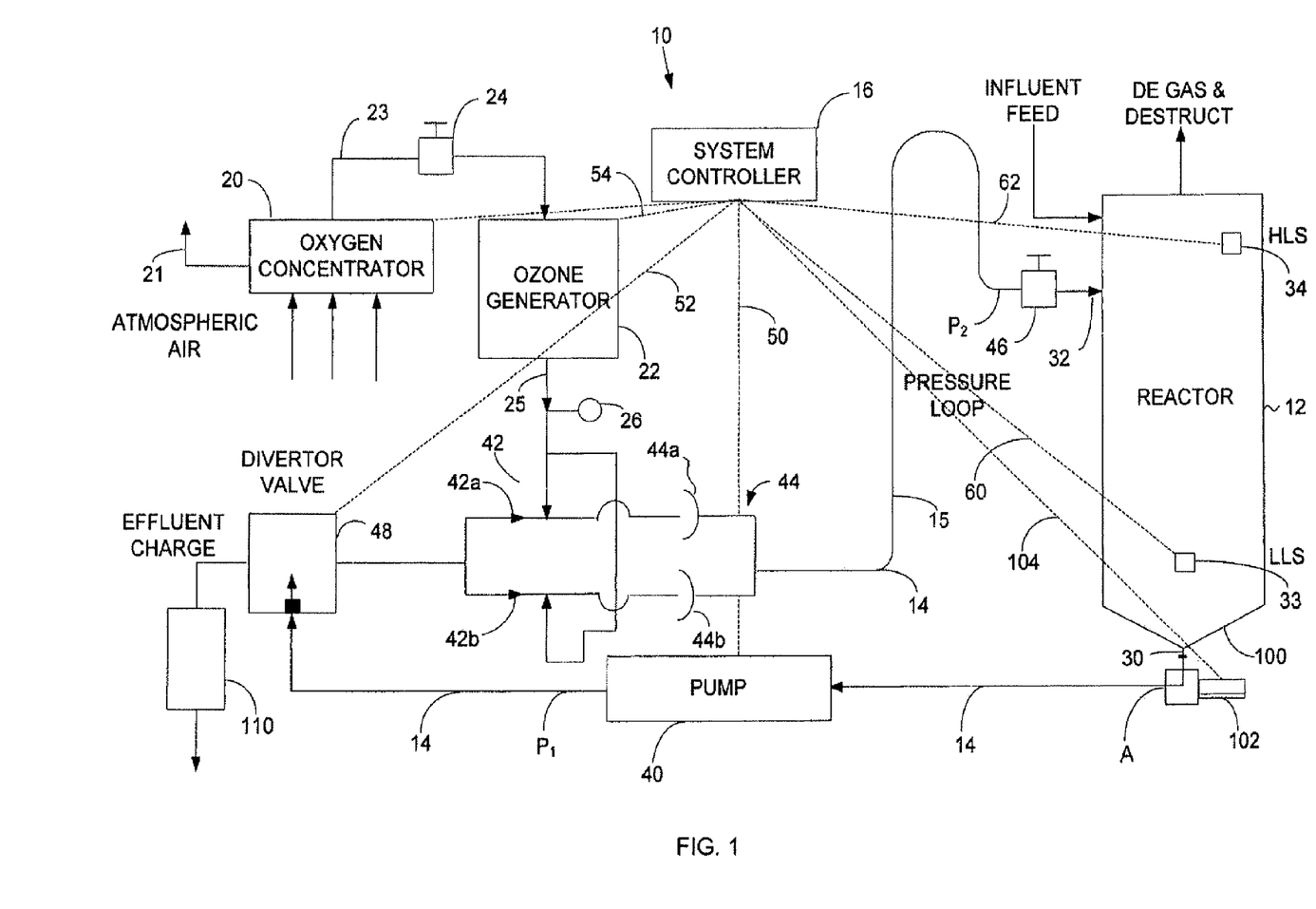
FIG. 1 is a schematic flow chart of a first apparatus in accordance with the invention.

FIG. 1 illustrates an apparatus in accordance with the invention. The treatment apparatus, illustrated in the schematic generally at 10, includes a processing tank (reactor) 12, a recirculation conduit 14 and a control system 16. The treatment apparatus 10 also includes an oxygen concentrator 20, and an ozone generator 22.

The recirculation conduit 14 is fluidly connected to a fluid outlet 30 from the processing tank (reactor). The recirculation conduit 14 is also connected to a fluid inlet 32 of the processing tank (reactor) 12. The recirculation conduit 14 further includes a pump 40. The pump 40 withdraws fluid to be treated from the processing tank (reactor) 12 and recirculates it, along the length of the recirculation conduit 14 and then reintroduces the fluid into the tank 12. In the embodiment illustrated herein, the pump 40 is sized so as to pump a quantity of fluid Q, at least equal to the amount of fluid contained within the processing tank (reactor) within not greater than five minutes. Other size pumps may be utilized in accordance with this invention, but a pump of this capacity has proven effective.

In order to maintain a fixed quantity of fluid in the tank at the time treatment is commenced, the processing tank (reactor) 12 includes a low level fluid sensor 33 and a high level fluid sensor 34. When a source of aqueous solution to be treated is obtained, it is transferred to the processing tank (reactor) until such time as the high level sensor senses that fluid level. Then, no more fluid is allowed into the processing tank (reactor) and the treatment process may thereafter begin on a batch process basis.

The recirculation conduit 14 further includes an ozone injector set 42, and a mixer set 44. The recirculation conduit 14 also includes a pressure device 46, in this case a valve. Advantageously the recirculation conduit 14 also includes a diverter valve 48. The diverter valve 48 may be utilized to control the passage of fluid from the pump 40 either for recirculation throughout the entire length of the recirculation conduit 14 or when switched, the diverter valve is redirected to permit discharge of treated fluid for after treatment collection or disposal.

The oxygen concentrator 20 is open to the atmosphere so as to draw in atmospheric air. The oxygen concentrator 20 may also be connected to sources of oxygen such as industrial grade and/or medical grade oxygen. For economic reasons, it is usually preferred to use atmospheric air as the input source to the oxygen concentrator. The oxygen concentrator separates most of the nitrogen, argon and humidity from the inlet air and the gases separated are given off through a vent 21. A typical oxygen concentrator which may be used is the Sequal Technologies Inc. model 1265. The oxygen concentrator is connected to an oxygen delivery conduit 23. The oxygen delivery conduit 23 passes through an oxygen flow control valve 24 and then into the ozone generator 22. The oxygen flow control valve is what is referred to as a "very fine metering" valve. An example is the model SS-SS4 valve available from SWAGELOK company. A useful ozone generator is the Simpson Environment model SW10M. The ozone generator 22 is connected to the inlet of the ozone injector set 42 by an ozone delivery conduit 25. Advantageously, ozone delivery conduit 25 includes a manometer 26 to measure vacuum pressure created at the suction port of the ozone injector set 42.

The controller 16 is electrically connected for control to the following components; control line 50 of the pump 40, control line 52 of the diverter valve 48, control line 54 of the ozone generator 22, control line 60 of the low water sensor 33, control line 62 of the high water sensor 34 and control line 104 of electrode 102.

The pump 40 withdraws fluid from the processing tank (reactor) 12 and delivers fluid downstream of the pump at a pump output pressure. The aqueous solution being treated then passes through the diverter valve 48, in the apparatus as shown, then through the ozone injector set 42. Advantageously, to enhance flow rates and good injection, the ozone injector set 42 may include one, two or more individual injectors 42a, 42b, etc. operating in parallel. An example used in the tests referred to herein is the model 584 from Mazzei Injector Corporation. As the fluid passes through the ozone injector set 42, a vacuum pressure is created at the venturi(s) of the ozone injector set 42, thus drawing ozone into the aqueous fluid. Ozone is mixed with the aqueous fluid in the ozone injector set 42. However, as the fluid passes along the recirculation conduct 14 downstream of the ozone injector set 42, it passes through the mixer set 44. An example of a suitable mixer is the Mazzei Injector Corporation model FR-75-X. Advantageously, the mixer set 44 includes a separate mixer 44a, 44b, etc. one for each ozone injector 42, 42b, etc. After passing downstream from the mixer set 44, the fluid being treated passes along a pressure portion 15 of the recirculation conduit 14, having considerable length. After passing through that pressure portion 15 of recirculation conduit 14, the aqueous fluid passes through the pressure device 46.

From reviewing the diagram and the above description, it will be noted that the fluid is under pressure delivered by the pump within the portion of the treatment conduit leading up to the ozone injector set and onward downstream to the pressure device 46. By adjustment of the pressure device 46, either manually or by a controller, significant back pressure is created, so that the pressure portion 15 of the treatment conduit extending from the ozone injector set 42 to the pressure device 46, is kept under a desirable pressure.

The time during which the aqueous solution to be treated, is kept under pressure while travelling from the ozone injector set 42 to the pressure device 46 is a function of the volume being pumped and the conduit cross section and the length of the portion 15 of recirculation conduit 14 from the ozone injector 42 to the pressure device 46. By making that pressure portion 15 of the recirculation conduit 14 longer for a given cross sectional area, then the aqueous fluid will be maintained under the desired pressure for a longer time on each recirculation pass.

The controller 16 controls the operation of the pump.

The process in accordance with the invention involves the treatment of the aqueous solution to be treated with ozone at higher than atmospheric pressure. We have discovered, that the effectiveness of the ozone treatment can be enhanced by ensuring better contact between the ozone and the aqueous solution to be treated. Ozone is a gas. The amount of gas that may be dissolved in a fluid increases with pressure. Thus, operating the portion of the recirculation conduit downstream of the ozone injector set at a pressure higher than atmospheric, helps to keep the ozone in intimate contact with the aqueous fluid and perhaps to dissolve the ozone within the aqueous fluid. We have discovered that increasing the pressure in the pressure portion 15 of the recirculation conduit 14 between the ozone injector set 42 and the pressure device 46 results in increased effectiveness of the treatment. Preferably, the pressure in the pressure portion 15 of the recirculation conduit 14 is greater than the partial pressure of the ozone at the ambient operating conditions. The higher the pressure in the pressure portion 15 the more ozone that can be dissolved. If the pressure in the pressure portion 15 is only at 0 gauge pressure and if atmospheric conditions are at low pressure, very little ozone injected may be dissolved in the aqueous solution.

In the tables set out below, solutions to be treated were obtained from a domestic sewage stream and an influent stream for a municipal sewage treatment plant. The municipal input stream includes sewage from domestic sources, commercial sources and industrial sources. The following tables illustrate various characteristics of the fluids before and after treatment. The following symbols have the following meaning. The symbol $BOD_5$ represents the biochemical oxygen demand of the fluid. CBOD is presented in milligrams per liter and reflects what is referred to as the carbonaceous (non-nitrogenous) biochemical oxygen demand of the fluid. The symbol TSS represents the total suspended solids in the solution. The symbol Total P represents the total phosphorus content of the solution. The symbol TKN (Total Kjeldahl Nitrogen) is a measure of the total nitrogen component of the solution. The symbol *E. Coli* refers to the *E. Coli* microorganism in the water.

In a first test, Table I, a system similar to that depicted in our previous patents, but with a filter, was used. Table I illustrates the enhanced treatment which occurs at 1½ A as compared to 1 ATM in the treatment conduit. The tests of Table I were done using influent domestic sewage.

An apparatus as depicted schematically in FIG. 1 was used for the tests set out in Tables II and III. The processing tank (reactor) 12 had a batch capacity of 60 liters. The pump 40 had a capacity to pump approximately 40 liters per minute. The ozone injector set 42 was made up of two Mazzei injectors operating in parallel. The ozone injector set 42 has a capacity to inject greater than 1.65 mg of ozone per liter of solution passing through each of the two injectors. The system was operated on a batch of aqueous solution for a continuous period of minutes. Thus, on average, the solution being treated, passed through the injector set about 20 times in 30 minutes.

A test on a second batch of municipal sewage influent was carried out at pressure of 1.5 ATM and 2 ATM in the pressure portion 15. See Table II. The pressure immediately upstream of the ozone injector set 42 was measured at 45 psi while the pressure immediately upstream of the pressure control valve was measured at 20 psi in the first run. Thus, the aqueous fluid was maintained under a pressure of about 1.5 ATM. In the second run, the pressure immediately upstream of the ozone injector set 42 was measured at 48 psi while the pressure immediately upstream of the pressure device 46 was measured at 28 psi. Thus, the aqueous fluid was maintained under a pressure of about 2 ATM in the pressure portion 15. Thus, Table II illustrates the improvement particularly in denutrification from increasing the pressure in the pressure section. A third test on a third batch of municipal sewage influent was carried out for 2 seconds and 12 seconds residence time in the pressure portion 15. See Table III. (Increased residence time occurred by increasing the length of the pressure portion 15 downstream of the ozone injector set 42). Table III shows the enhanced denutrification with greater residence time.

We have surprisingly found that recirculation of the aqueous fluid to be treated, through the ozone injector set 42, using the pressure processes outlined above has produced very substantial reductions in $BOD_5$ CBOD and TSS. Additionally, there has been a substantial reduction in total phosphorus and total nitrogen.

TABLE I

| PARAMETER | PERCENTAGE REDUCTION | |
|---|---|---|
| | 1 A | 1½ A |
| $BOD_5$ | 85.0% | 88.5% |
| CBOD | 61.0% | NR |
| TSS | 92.0% | 97.0% |
| TP | 38.0% | 94.8% |
| TKN | 27.0% | 79.5% |

TABLE II

| PARAMETER | PERCENTAGE REDUCTION | |
|---|---|---|
| | 1½ A | 2A |
| $BOD_5$ | 56% | 81% |
| CBOD | 61% | 69% |
| TSS | 83% | 94% |
| TP | 28% | 60% |
| TKN | 11% | 49% |

TABLE III

| PARAMETER | PERCENTAGE REDUCTION | |
|---|---|---|
| | 2 sec | 12 sec |
| $BOD_5$ | 84% | 94% |
| CBOD | 83% | 92% |
| TSS | 98% | 99% |
| TP | 66% | 89% |
| TKN | 17% | 39% |

At the outset of the test shown in Table III, the *E. Coli* of the test solution in the first test measured in excess of 300,000. This had been reduced to a count of less than 2 after 30 minutes of continuous recirculation through the recirculation conduit of the apparatus referred to above. This represents a 99.999% reduction in *E. Coli*, or a five log disinfection of the fluid.

The reduction of *E. Coli*, illustrates that the disinfection of the fluid is not reduced in any way when carrying out the present invention and is probably enhanced from what might have been expected from our earlier work. The above tests clearly show that, surprisingly, maintaining the fluid being treated under pressure above atmospheric, and for a longer period of time, each enhance the treatment effect.

Denutrification as used in this application is a term used to describe the reduction of nutrients in an aqueous solution. The nutrients include both biological and chemical organic compounds and elements. Useful measures of these nutrients include Biochemical Oxygen Demand ($BOD_5$), Carbonaceous (Non-Nitrogenous) Biochemical Oxygen Demand (CBOD), and Total Suspended Solids (TSS). Included in these measures are the elements, phosphorus and nitrogen, which are measured as Total Phosphorus (TP), and Total Kheldahl Nitrogen (TKN). These elements are of particular interest because they have a significant uptake of dissolved oxygen.

Denutrification may be accomplished by advanced oxidation using ozone. This process is manifested in a number of ways.

a) Complete Oxidation—the change of complex compounds and elements into different form by satisfying their oxygen demands, for instance, altering the nature of phosphorous compounds, i.e. altering bound phosphorus compounds or ammonia can be broken down to nitrogen, oxygen and water according to the reaction: $2NH_4OH+3O_3 \rightarrow N_2 + 5H_2O+3O_2$ b) Partial Oxidation—the change of complex compounds by molecular damage rendering them vulnerable to further change c) Off Gassing—this is in particularly applicable to nitrogen, $N_2$ d) Microfloculation—these are collections of particulate which remain suspended in solution e) Precipitation—these are again collections of particulate which do not remain in solution.

Oxidation of phosphorous and nitrogen compounds produces microflocs and precipitates which may include phosphates, orthophosphates, nitrates, nitrites, etc. The ozone does not react directly with phosphorous but with compounds of phosphorous.

Upon discharge, the microflocs and precipitates referred to above may be captured by a multi-gradient filter 110 before release to the environment. An example of a useful filter is the twenty-five to five (25-5) micron pre-filter, 20 inch high heavy duty filter sold under the trade mark Pentek Big Blue (25-5).

The above tests show that maintaining a mixture of aqueous solution to be treated and ozone under a pressure of at least one and a half atmospheres, and more preferably, 2 atmospheres, results not only in a very highly desired disinfection but also very substantial reduction in phosphorus and nitrogen as well as $BOD_5$ and CBOD of the treated fluid. This is referred to generally as denutrification. The level of denutrification achievable by this process is remarkable.

Ozone Amount Optimization

We have found that even more remarkable results can be achieved in a shorter operating time by ensuring that an optimal amount of ozone is injected as the system operates. As the system operates, there is a continual input of energy to the solution being treated arising from the operation of the circulating pump. Passage through various of the components in the recirculation conduit and perhaps the treatment tank itself, all add to the energy level of the fluid. Thus, as might be expected, during tests of this type, the temperature of the fluid tends to increase as the circulation time increases. Increasing temperature, increases the difficulty of introducing ozone into the aqueous solution so as to at least partially dissolve the ozone. We have also discovered, that the total amount of gas being introduced into the aqueous solution by the ozone injector remains a factor. Thus, if the gas being injected by the ozone injector has other components other than ozone, such as either oxygen or nitrogen, then the amount of ozone being injected will not be optimized.

We have found a system and process for optimizing the ozone injection. For any given ozone generator 22, there will be a maximum amount of ozone that can be produced. In the case of the model SW10M referred to above we determined that this was 5.50 standard cubic feet per hour (SCFH). With this information, then the oxygen flow control valve 24 is adjusted to provide exactly the amount of oxygen from the oxygen concentrator to produce the desired flow of 5.50 SCFH ozone. The next step is to adjust the suction pressure at the ozone injector set 42. This can be done with the aid of a manometer 26. The system is adjusted so that the suction at the injector set produces a suction of 5.50 SCFH of ozone. This is achieved by adjusting the pressure device 46 which may be done by manual control. Advantageously the back pressure created by the pressure device 46 creates a back pressure of approximately 25 psi which is in the range of 1.5 to 2.0 atmospheres. The above adjustments may be made using the manometer 26 in the first instance connected in a flow mode and in a second instance connected in the suction mode.

While the above figures are specific to the system utilized in the apparatus discussed in detail herein and in particular the SW10M model ozone generator, this system can be utilized more generally to optimize the operation of any apparatus as discussed herein.

We have found, that feeding too little oxygen to the ozone generator 22, will result in less than an optimum level of ozone generated, with the negative effect that the gas being injected at the ozone injector 42 will have a higher than desirable nitrogen component. The nitrogen component then reduces the amount of ozone that may be dissolved in the circulating fluid. On the other hand, feeding too much oxygen from the oxygen concentrator 20, delivers more oxygen to the ozone generator 22 than the ozone generator 22 is capable of handling. This results in an excess of oxygen in the gas to be injected through the ozone injector set 42. Again this reduces the potential for optimized ozone injection. Thus, the oxygen flow control valve 24 is adjusted to optimize the flow of oxygen from the oxygen concentrator 20 so as to give the optimized performance characteristics of the ozone generator 22 and in turn to optimize the amount of ozone that may be dissolved in the circulating fluid.

While the above tests and disclosure show the advantages and potential for treating influent streams as discussed above, one of the aspects of any such treatment system, is to provide a monitoring system so as to show that the desired level of treatment has been achieved. As the influent may differ rather dramatically in content, from influent streams that are relatively easily treated such as domestic sewage to streams having a different content which may be much more difficult to treat including commercial and industrial waste, different processing times may be required depending upon the nature of the influent and the desired characteristics of the system effluent. As a first level of desirability, it is often first required that the influent be treated to the level at which there is reasonable confidence that disinfection to the desired extent has occurred. In other situations, it may be desirable to ensure that the fluid being treated has been treated to a level of denutrification as may be desired.

We have discovered by taking readings, that the oxidation/reduction potential (ORP) of the fluid rises during processing. The change in ORP can be correlated to the oxidation level of the fluid being treated. Our initial analysis shows that light domestic sewage often has a ORP of +50 mV prior to processing. Fluids requiring substantially more processing such as heavy municipal sewage which may include industrial and commercial components, will often have a ORP of −350 mV. On the other hand, as the fluid is oxidized, the ORP will rise to much higher voltages. De-chlorinated, de-ionized test water has often been shown to have an ORP of +200 mV. Chlorinated municipal water will often have an ORP of +350 mV.

At an ORP of +650 mV, bacteria will have been killed virtually instantaneously. This figure has been reported by the World Health Organization as a figure indicative of an ORP at which all bacteria has been killed. Through testing to date, we have determined that there is a very substantial denutrification, when the ORP rises to about +800 mV.

Accordingly, we have devised a process monitoring system for use with the system as outlined above. A suitable monitoring system, advantageously, monitors what is the worst quality liquid leaving the processing tank 12. Advantageously, the processing tank includes a conical shaped bottom as diagrammatically indicated at 100 in FIG. 1. The advantage of the conical bottom is that if there is any sediment or other unusual flow patterns within the processing tank 12, the fluid being processed and withdrawn from the apex of the conical bottom 100 will contain as much sediment or other material to be treated as may be contained within the processing tank 12. This helps to circulate any solids or other materials which might otherwise collect if the processing tank had a flat bottom.

In order to monitor the system, an electrode 102 is installed in the portion of the recirculation conduit 14 between the processing tank 12 and the recirculation pump 40. Locating the electrode 102 in this portion of the recirculation conduit helps to ensure that the electrode measures the condition of the influent being processed at the least desirable portion of the treatment conduit. If the electrode were to be installed in the pressurized section 15 of the recirculation conduit, then the electrode is more likely to give an erroneously beneficial reading. As the process will involve withdrawing influent from the processing tank 12 through the pump 40 and then sending to discharge, it is recommended that the electrode 102 for monitoring purposes be placed upstream of the pump and downstream of the processing tank 12 as illustrated in the FIG. 1.

Advantageously, a twin platinum electrode may be used. The electrode sends a signal to an ORP controller. One such instrument is available from Pulse Instrument bearing the model designation 117E. This is an example of an acceptable meter/controller. The controller function for the electrode 102 as illustrated in FIG. 1 may be a separate controller or may be part of the control 16 illustrated in FIG. 1. The electrode 102 communicates with the control 16 through control line 104.

When the system is operating, the electrode 102 will provide continuous voltage readings monitoring the fluid passing along the treatment conduit up stream of the pump 40. At the outset of the treatment process, the ORP may be negative or slightly positive, depending upon the nature of the influent being treated. As the influent circulates and is processed and as ozone is injected into the influent, all as explained above, the monitored voltage will be seen to rise. Depending upon the nature of the influent and the level of treatment required, the time to process the fluid to a desired level will vary.

As set out above and as recognized by the World Health Organization, once the ORP rises to a consistent reading of 650 mV, there is sufficient confidence that any bacterial content in the fluid will have been killed. Thus, once a consistent reading of 650 mV is achieved, the fluid can be discharged if that is the desired treatment level. As the fluid readings may vary slightly during treatment, a more convenient way of monitoring the system is to continue to process the fluid circulating until the reading is consistently above the 650 mV level say, for example, 675 mV. By selecting the 675 mV level there is better assurance that all portions of the fluid have been processed to at least the 650 mV level desired. Such a processed fluid would then have been disinfected to a desired level.

Where the treatment desired includes significant de-nutrification, the processing may be continued until the ORP of the treated fluid rises to a consistency of substantially 800 mV.

Table IV sets out an example of a fluid which at the outset is de-chlorinated, de-ionized test water. The ORP measured in mV at time zero was +118 mV. As set out in the table, the ORP rose through 185 mV after one minute, 383 mV after two minutes and 910 mV after four minutes.

Table V includes the data for a similar test in which the fluid to be treated was obtained from a municipal sewage plant. At the outset the ORP measured +380 mV The table shows that the ORP rose to over 800 by fifteen minutes and that further processing did not substantially increase the ORP reading. Thus, for all practical purposes the processing to achieve disinfection and, denutrification to an acceptable state had been successfully concluded after twenty minutes. Although the fluid measured was obtained from a municipal sewage plant, the ORP measurement of +380 mV is misleadingly high. In the system discussed herein, the system has a capacity of 60 liters in the treatment tank. However the controls are set so as to treat a batch and then dispose of 40 liters that have been treated. In the case of this particular example, the previous batch treated had been dechlorinzed, deionized water which had an ORP of +910 mV following processing. As only 40 liters of that batch were disposed of, the equipment contained 20 liters of water having an ORP of +910 to which was mixed the sewage influent. In this particular case, the reading of +380 mV was the analysis of the mixed fluid comprising 40 liters of sewage and 20 liters of the ionized water. Upon realizing this error in the readings, all other readings referred to in this application measure the influent prior to being transferred into the processing tank.

Tables VI and VII illustrates the values for a repeat test done a few weeks after the tests referred to above. Again the first test was carried out with dechlorinated, deionized test water, while the second test was carried out using a sample obtained from a municipal sewage collection system.

As set out in Table VI, with respect to dechlorinated deionized water, the ORP rose from a starting value of +100 to a value of +600 within four minutes. In Table number VII, the meter measured an ORP value for the municipal sewage at the outset at −200 mV and a reading of +650 mV was obtained after twenty-two minutes of processing.

The above experiments were repeated for a third time, again using de-chlorinated, de-ionized test water and municipal sewage. The test results for the third test using de-chlorinated, de-ionized test water are set out in Table VIII which shows that the ORP has risen to +806 after four minutes. The test procedures for sewage when carried out the third time are set out in Table IX which show that the ORP goes from 28 at the outset for the municipal sewage to a reading of 800 mV after approximately twenty-seven minutes. Further processing for approximately a total time of thirty-five minutes raised the ORP to 810.

TABLE IV

| METER No. | PSI | INJECTOR | SUCTION (SCFH) | MEASUREMENT POINT | TIME (MINS) | OZONE RESIDUAL (mg/L) | TEMP °C. | ORP (mV) |
|---|---|---|---|---|---|---|---|---|
| 1 | 48 | | | | | | | |
| | | #584 | 2.750 | A | 0 | 0.00 | 15.5 | 118 |
| 2 | 25 | | | | | | | |
| | | | | | 1 | 0.11 | 15.5 | 185 |
| | | | | | 2 | 1.14 | 15.8 | 383 |
| | | | | | 4 | 1.60 | 16.1 | 910 |

TABLE V

| METER No. | PSI | INJECTOR | SUCTION (SCFH) | MEASUREMENT POINT | TIME (MINS) | OZONE RESIDUAL (mg/L) | TEMP °C. | ORP (mV) |
|---|---|---|---|---|---|---|---|---|
| 1 | 48 | | | | | | | |
| | | #584 | 2.750 | P | 0 | 0.00 | 13.5 | 380 |
| 2 | 25 | | | | | | | |
| | | | | | 5 | 0.18 | 14.9 | 525 |
| | | | | | 10 | 0.00 | 15.3 | 782 |
| | | | | | 15 | 0.00 | 16.4 | 811 |
| | | | | | 20 | 0.00 | 17.6 | 826 |
| | | | | | 25 | 0.05 | 18.7 | 841 |
| | | | | | 30 | 0.00 | 19.9 | 852 |
| | | | | | 35 | 0.10 | 21.1 | 865 |
| | | | | | 40 | 0.00 | 22.0 | 873 |

TABLE VI

| METER No. | PSI | INJECTOR | SUCTION (SCFH) | MEASUREMENT POINT | TIME (MINS) | OZONE RESIDUAL (mg/L) | TEMP °C. | ORP (mV) |
|---|---|---|---|---|---|---|---|---|
| 1 | 48 | | | | | | | |
| | | #584 | 2.750 | A | 0 | 0.00 | 20.8 | 100 |
| 2 | 25 | | | | | | | |
| | | | | | 1 | 0.28 | 21.3 | 125 |
| | | | | | 2 | 0.83 | 21.7 | 218 |
| | | | | | 4 | 1.65 | 22.3 | 600 |

TABLE VII

| METER No. | PSI | INJECTOR | SUCTION (SCFH) | MEASUREMENT POINT | ORP (mV) | OZONE RESIDUAL mg/L | TEMP (° C.) | TIME (MINS) |
|---|---|---|---|---|---|---|---|---|
| 1 | 46 | #584 | 2.750 | P | −200 | 0.00 | 16.5 | 0 |
| 2 | 25 | | | | +650 | 0.00 | 24.5 | 22 |

TABLE VIII

| METER No. | PSI | INJECTOR | SUCTION (SCFH) | MEASUREMENT POINT | TIME (MINS) | OZONE RESIDUAL mg/L | TEMP (° C.) | ORP (mV) |
|---|---|---|---|---|---|---|---|---|
| 1 | 47 | #584 | 2.750 | A | 0 | 0.00 | 18.8 | 135 |
| 2 | 25 | | | | 1 | 0.05 | 19.4 | 173 |
| | | | | | 2 | 0.30 | 19.9 | 290 |
| | | | | | 4 | 1.22 | 20.4 | 806 |

TABLE IX

| METER No. | PSI | INJECTOR | SUCTION (SCFH) | MEASUREMENT POINT | ORP (mV) | OZONE RESIDUAL mg/L | TEMP (° C.) | TIME (MINS) |
|---|---|---|---|---|---|---|---|---|
| 1 | 45 | #584 | 2.750 | P | 28 | 0.00 | 14.2 | 0 |
| 2 | 25 | | | | 650 | 0.36 | 18.3 | 7:36 |
| | | | | | 700 | 0.34 | 19.8 | 9:53 |
| | | | | | 750 | 0.27 | 20.2 | 14:14 |
| | | | | | 800 | 0.27 | 22.6 | 27:10 |
| | | | | | 810 | NR | 26.0 | 35:00 |

These figures and tables as set out above, illustrate that an appropriate system for monitoring the above-noted process and system can be achieved by monitoring the ORP of the fluid under processing. The above figures, when correlated, establish many things required in the verification process. Accordingly, if any element in the apparatus is not working, for example, the oxygen concentrator, the ozone generator, or the pump, then there will not be the desirable increase in the ORP. With the ORP increasing as indicated above, this provides verification that the components of the system are, in fact, working and that suitable processing is occurring. In addition to monitoring that the system components are working as intended, this also provides a signal, indicative of processing to a given level. Once the processing to the desired level is achieved, then the controller can use that information to operate the discharge valve so as to permit discharge of the fluid from the processing system. Once the batch has been discharged, then a new batch may be introduced into the processing tank and the system begins to operate to process a subsequent batch.

The system, apparatus and processes described herein are useful for the treatment of a wide variety of influents and for a wide variety of purposes. Influent streams such as those from a household do not normally contain any chemicals and therefore present an influent solution which is relatively easy to clean up. The system apparatus and processes described herein are directly competitive with and provide a significantly desirable alternative to the use of septic tanks and tile bed disposal systems. For individual household locations remote from city operated sewer systems, the system, apparatus and processes described herein are particularly well adapted for use in place of a septic tank. The effluent leaving a private residence may be collected in a tank which essentially forms a buffer/storage tank. The system can then be operated in a batch process to process the sewage where it may be disposed of in a bed. Where routinely, septic tank systems have only resulted in disinfection to a level of, perhaps, at best, two log disinfection, the present system is easily able to achieve a much higher level of disinfection, perhaps at least a four log reduction.

The present system, apparatus and processes may also be used to treat water for irrigation purposes. Again, the influent may be extremely variable with respect to the contents of the influent. When the treated solution is to be used for surface irrigation, then typically, standards set by governmental agencies, for example, the U.S. EPA or Environment Canada must be met. The system, apparatus and processes of the present invention are able to achieve a five log disinfection relatively easily when the influent is household sewage.

When using the system, apparatus and processes explained above, there is an optional choice as to whether the treated fluid is to be deneutrified or not. In the case of fluid being used for irrigation, the nitrogen and phosphorus components in the fluid may be advantageously used by the plants being irrigated. Where that is the intended use of the system, apparatus and process, there is no need and perhaps a desire not to attempt to remove nitrogen or phosphorus from the treated effluent. In these cases, then, the filter would desirably be eliminated from the disposal line as it is the action of the filter which results in the reduction of phosphorus compounds in the effluent. Similarly, where the nitrogen is a desired component of the effluent, then off gassing may not be desirable.

On the other hand, where processing of household sewage and the like, particularly in remote areas near watersheds, is desirable, in and of itself, removal of nitrogen and phosphorus from the treated effluent becomes particularly important as a factor in helping to maintain the quality of the local water shed. In these cases, the system, apparatus and process can advantageously involve a degasification as explained above to promote nitrogen removal from the treated effluent and also passing the treated effluent through the filter described above so as to promote removal of phosphorus. As shown by the tables referred to hereinbefore, the system, process and apparatus can provide a significant reduction in nitrogen and phosphorus content in the treated filtered effluent.

All of the tests referred to in the foregoing discussion were performed using a test apparatus in which the amount of fluid in the reactor or batch tank was circulated through the ozone injectors in approximately one and a half minutes. When the system is operated for 30 minutes this involves approximately 20 passes for the batch, on average, through the ozone injectors. The amount of time this system must be operated, or perhaps more accurately the number of passes required, will depend on at least two factors. One of these is the quality of the influent, that is how much clean up is required, and secondly, what is the quality desired of the treated effluent. In all cases, the ozone input to the fluid and thus the treatment cycle must continue long enough so that the biochemical oxygen demand ($BOD_5$) is satisfied by the ozone and that sufficient additional ozone injection occurs to reach the desired disinfection and/or denutrification level.

Figure 2:
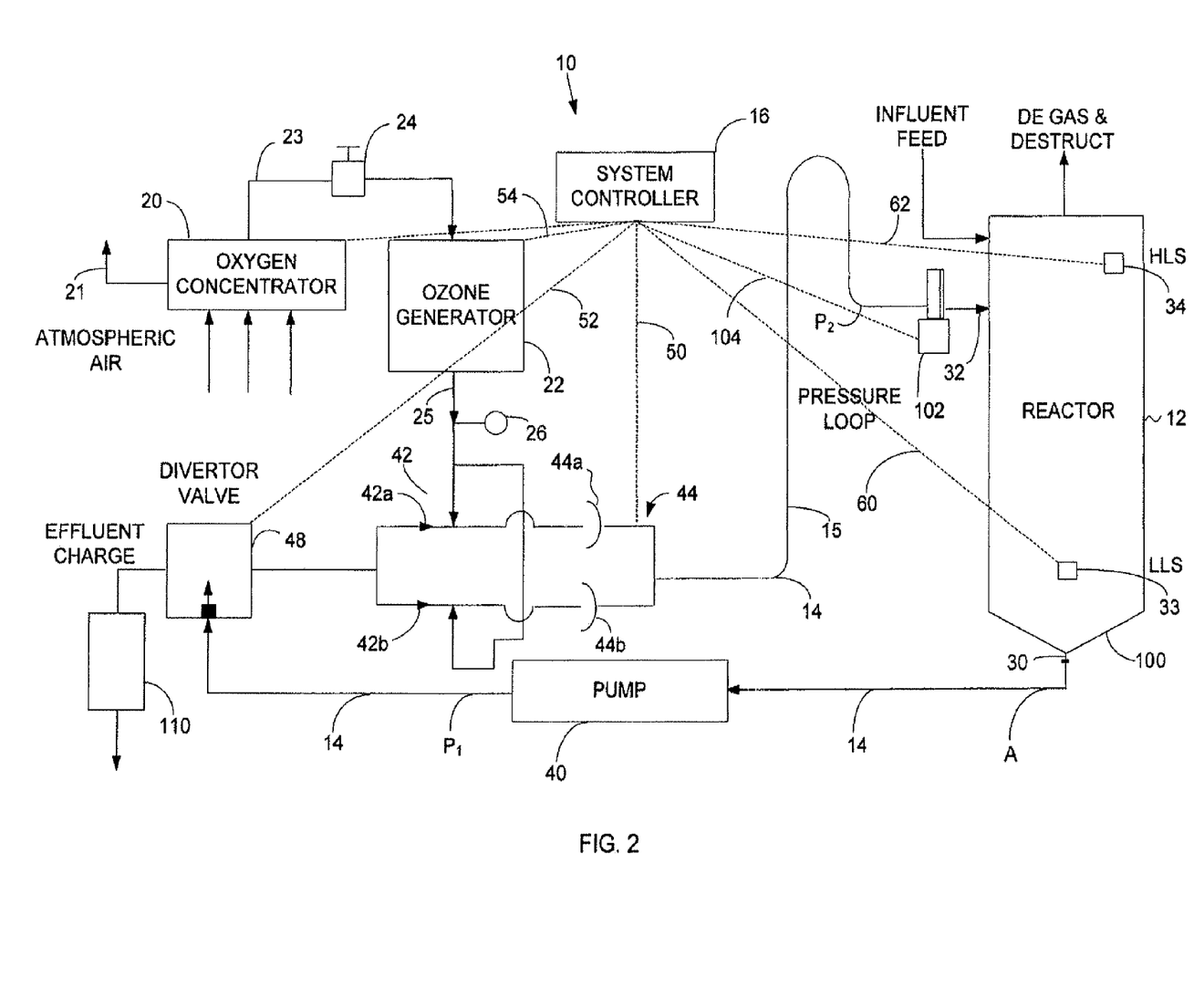
FIG. 2 is a schematic flow chart of a second apparatus in accordance with the invention.
Figure 3:
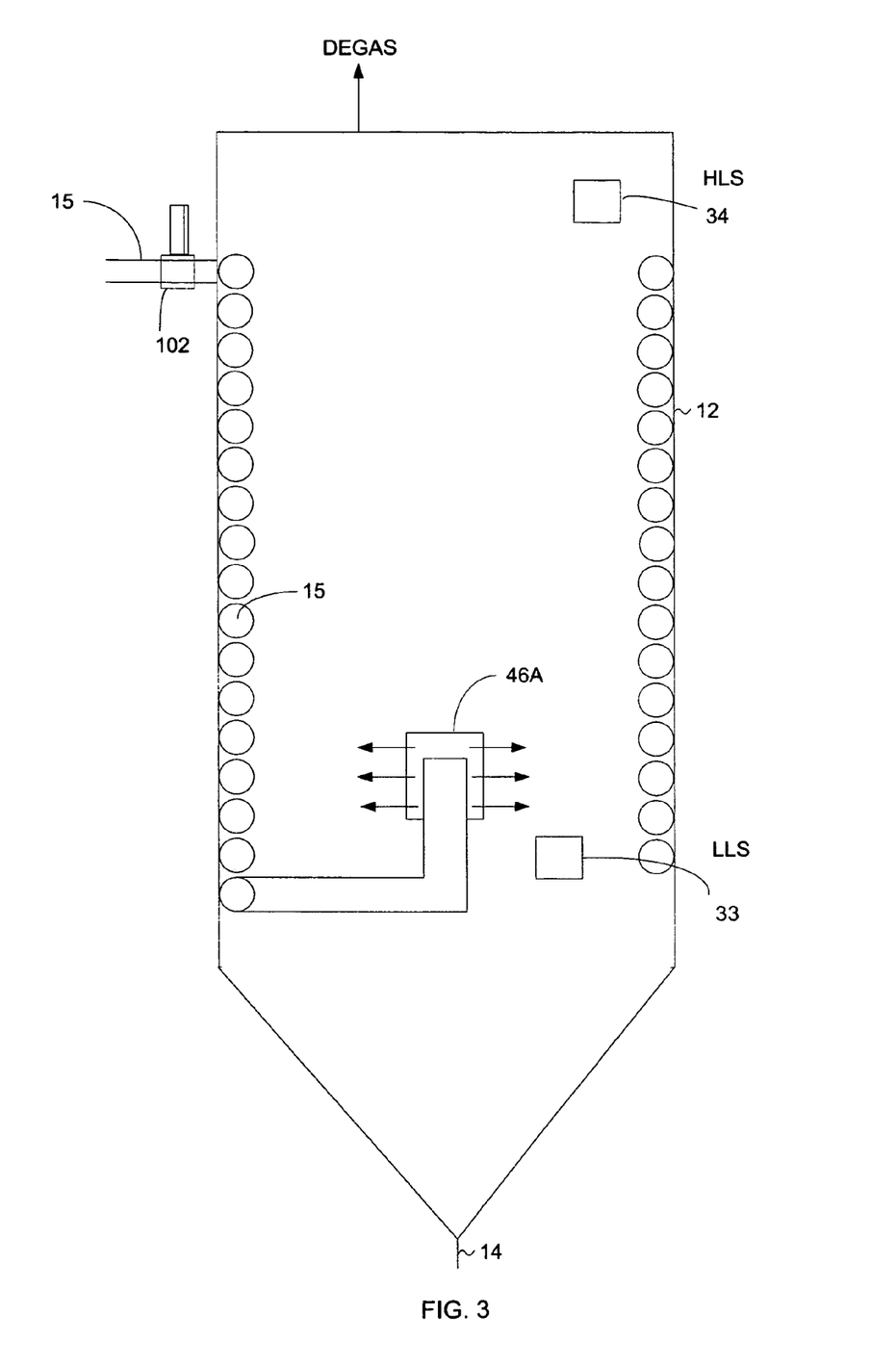
FIG. 3 illustrates a portion of the apparatus of FIGS. 1 and 2 but in accordance with a further embodiment of the invention.

As illustrated in both FIGS. 1 and 2, the pressure portion 15 of the treatment conduit 14 comprises a section downstream of the pump to the pressure device 46. As explained above, in the embodiment illustrated in both FIGS. 1 and 2, the pressure device used was a simple control valve. By manually adjusting that valve, the desired pressure in the pressure section 14 was maintained. As explained above, when it was desired to have a longer pressure portion 15, then the length of the tubing forming the pressure portion 15 was greatly expanded. It happened to be convenient in the test apparatus being used, that the additional length of pressure loop could be comprised of a coil placed within the reactor 12 as shown in FIG. 3. By placing the additional length within the tank 12, the pressure valve 46 was eliminated. With the additional length of the pressure section within the reactor, the outlet from the pressure portion 15 was comprised of a back-pressure-causing orifice member 46A which then functions as the pressure device 46. The orifice member 46A is referred to herein as a restrictor/diffuser. That restrictor/diffuser included a fitting have a plurality of orificies. The outlet area of the orificies was calculated so as to restrict the flow in the pressure portion 15 to provide the desirable back pressure so as to maintain a pressure upstream of the restrictor/diffuser in excess of one atmosphere and where indicated, up to two atmospheres. Thus, the pressure device 46, instead of being a valve exterior to the treatment tank 12, comprised the back pressure causing restrictor/diffuser 46A.

Figure 4:
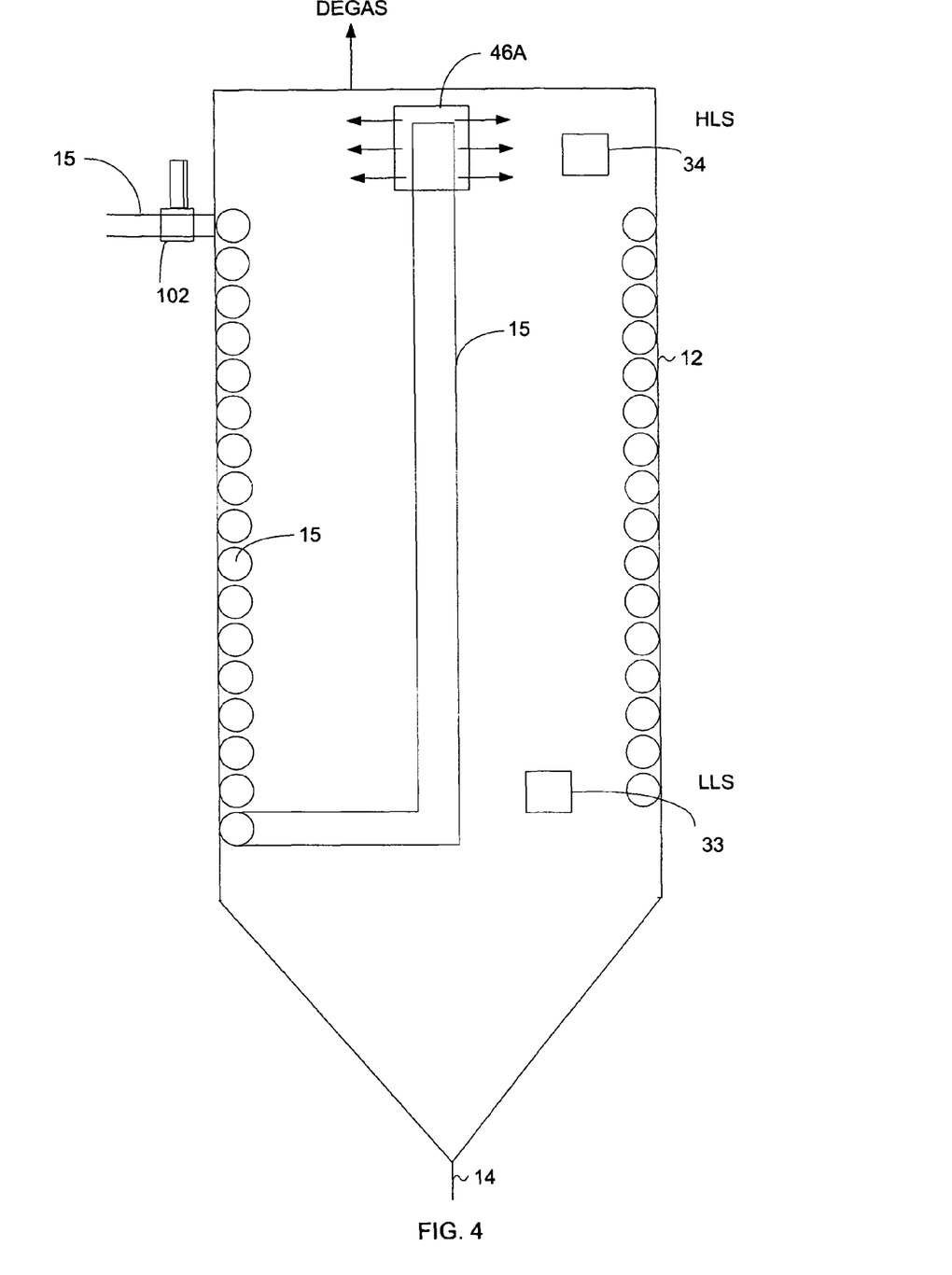
FIG. 4 is a view similar to FIG. 3 illustrating a further embodiment of the invention.

The restrictor/diffuser 46A could be positioned below the operating liquid level as shown in FIG. 3 or above the operating liquid level as shown in FIG. 4.

From our tests it appears that there is a greater release of off gases when the restrictor/diffuser is located above the operating liquid level within the tank 12 The restrictor/diffuser when located above the liquid seems to promote degasification of the treated fluid leaving the pressure section. From our tests we note that disinfection seems to be more readily obtainable with the restrictor/diffuser above the operating liquid level (FIG. 4). Our tests also, however, seem to show increased levels of denutrification are achieved with the restrictor/diffuser below the operating liquid level (FIG. 3).

In FIG. 1 the ORP sensor is located immediately adjacent the outlet of the tank. As stated above, this provides a sensing of the treated fluid at what is likely to be its worst condition. This location is particularly advantageous when the system, apparatus and process of this invention is being utilizing primarily for denutrification purposes. In FIG. 2, the ORP sensor is located within the recirculation conduit, pressure section, downstream from the ozone injectors but upstream of the pressure device. Advantageously this should be as close to the pressure device as is convenient. The reason for this location is that where de-gassing occurs, several gases will be given off during the de-gassing. There may be gasses formed in the recirculation conduit as a result of the ozone in the conduit. Thus, during the de-gassing, particularly where the pressure device is located above the fluid level in the treatment tank (reactor) it may be that ozone will be de-gassed as well as other gases. As an ORP sensor senses the level of disinfection component within a fluid, then locating the sensor as shown in FIG. 1, will give an unacceptably low reading and may not be satisfactorily indicative of the state of the fluid itself. Accordingly, when disinfection is the more important result of the process, it is suggested that the sensor be located upstream from the pressure device, within the recirculation conduit and the restrictor/diffuser be located above the liquid level of the tank.

The invention claimed is:

1. A batch process for the treatment of an aqueous sewage solution, said batch process comprising:
   obtaining an influent batch of aqueous sewage solution for treatment, said batch of aqueous sewage solution having a batch size volume, and said batch of aqueous sewage solution having a phosphorus content prior to disposal,
   treating said batch of aqueous sewage solution by an advanced oxidation and denutrification process, said advanced oxidation and denutrification process including causing ozone to be mixed with said aqueous sewage solution, said ozone acting on said aqueous sewage solution to decrease the BOD thereof;
   providing a treatment tank for holding said batch of aqueous sewage solution, a recirculation conduit fluidly connected to said treatment tank at an inlet and an outlet, said recirculation conduit having an ozone injector, and a pump mounted to said recirculation conduit, said pump being operable to urge flow of said batch of aqueous sewage solution through said recirculation conduit, said batch of aqueous sewage solution thereby being urged past said ozone injector,
   said oxidation and denutrification process including continuously recirculating the batch of aqueous sewage solution through the recirculation conduit and continuously injecting ozone into the batch of aqueous sewage solution as the batch of aqueous sewage solution recirculates through the ozone injector,
   the advanced oxidation and denutrification process including providing a pressure portion of said recirculation conduit downstream of the ozone injector, maintaining said pressure portion of said recirculation conduit at a higher pressure than said treatment tank, said pressure portion being maintained at a selected gauge pressure of at least one and a half atmospheres, and maintaining a selected residence time of said aqueous sewage solution passing through said pressure portion of at least 2 seconds in said pressure portion, said ozone engaging said aqueous sewage solution during said residence time;

continuously returning said aqueous sewage solution from said pressure portion to said treatment tank, and continuously recirculating the batch of aqueous sewage solution, for a recirculation time of at least 5 minutes before disposal, said recirculating including operating said pump to pump a flow volume of at least three and one third times the batch size volume during said batch process, whereby said batch of aqueous sewage solution urged through said recirculation conduit by said pump is repeatedly pressurized and depressurized during treatment thereof:

filtering said batch of aqueous sewage solution after said recirculation time to reduce the phosphorus content of said treated batch of aqueous sewage solution; and disposing of said treated batch of aqueous sewage solution, after said filtering.

2. The process of claim 1 wherein said aqueous sewage solution is maintained at a selected pressure of at least 1.5 atmospheres for a selected residence time of at least 6 seconds in said pressure portion.

3. The process of claim 2 wherein said aqueous sewage solution is maintained at a selected pressure of at least 1.5 atmospheres for a selected residence time of at least 12 seconds, in said pressure portion.

4. The process of claim 2 wherein the influent batch of aqueous sewage solution comprises a nitrogen content prior to treatment, and the process further comprises off gassing nitrogen gasses as said batch of aqueous sewage solution recirculates, said off gassing of nitrogen occurring from outside of said pressure portion of said recirculation conduit.

5. The process of claim 1 wherein said aqueous sewage solution is maintained at a selected pressure of at least 2.0 atmospheres for the selected residence time of at least 2 seconds, in said pressure portion.

6. The process of claim 1 wherein the process is carried out in a system having an oxygen concentrator connected to an ozone generator through an oxygen conduit, the oxygen conduit having an oxygen flow control valve and said process comprises controlling the flow of oxygen to said ozone generator to maximize the amount of ozone produced while minimizing the amount of oxygen and/or nitrogen downstream of the ozone generator.

7. The process of claim 1 wherein said batch of aqueous sewage solution is continuously recirculated for a total time of at least thirty (30) minutes before disposal.

8. The process of claim 1 the process including degassing of said treated aqueous sewage solution, downstream of said pressure portion of said recirculation conduit, and removing said degassed gasses.

9. The process of claim 1 wherein said recirculation conduit includes a sensor to sense the oxidation/reduction potential of the aqueous sewage solution, the process further comprising continuously circulating the aqueous sewage solution through the recirculation conduit and through the ozone injector, until the ORP of the treated aqueous sewage solution rises to a predetermined level.

10. The process of claim 9 wherein the processing is continued until the ORP is at least +650 mV.

11. The process of claim 9 wherein the processing is continued until the ORP is at least +675 mV.

12. The process of claim 9 wherein the process is continued until the ORP is at least +800 mV.

13. The process of claim 1 wherein the pump is selected and operated so as to pump a flow volume equal to at least 10 times the batch size volume during said process.

14. The process of claim 1 wherein the pump is selected and operated so as to pump a flow volume equal to at least 13 times the batch size volume during said process.

15. The process of claim 1 wherein the pump is selected and operated so as to pump a flow volume equal to at least 20 times the batch size volume during said process.

16. A batch process for the treatment of an aqueous sewage solution, said batch process comprising:

providing a treatment tank for holding a batch of aqueous sewage solution, a recirculation conduit fluidly connected to said treatment tank at an inlet and an outlet, said recirculation conduit having an ozone injector, and a pump mounted to said recirculation conduit, said pump being operable to urge flow of said batch of aqueous sewage solution through said recirculation conduit, said batch of aqueous sewage solution thereby being urged past said ozone injector, establishing said batch of aqueous sewage solution for treatment in the treatment tank, said batch of aqueous sewage solution having a batch size volume;

treating said batch of aqueous sewage solution by an advanced oxidation and denutrification process, said advanced oxidation and denutrification process including causing ozone to be mixed with said aqueous sewage solution, said ozone acting on said aqueous sewage solution to decrease the BOD thereof;

said oxidation and denutrification process including recirculating the batch of aqueous sewage solution through the recirculation conduit and continuously injecting ozone into the batch of aqueous sewage solution while doing so;

the advanced oxidation and denutrification process including providing a pressure portion of said recirculation conduit downstream of the ozone injector, maintaining said pressure portion of said recirculation conduit at a higher pressure than said treatment tank, said pressure portion being maintained at a selected gauge pressure of at least one and a half atmospheres, and maintaining a selected residence time of said aqueous sewage solution passing through said pressure portion of at least 2 seconds in said pressure portion, said ozone engaging said aqueous sewage solution during said residence time;

continuously returning said aqueous sewage solution from said pressure portion to said treatment tank, and continuously recirculating the batch of aqueous sewage solution, said recirculating including operating said pump to pump a flow volume of at least three and one third times the batch size volume during said batch process, so that said batch of aqueous sewage solution urged through said recirculation conduit by said pump is repeatedly pressurized and depressurized during treatment of thereof.

17. The process of claim 16 wherein said process includes filtering said aqueous sewage solution after said recirculating, to reduce the phosphorus content of said treated aqueous sewage solution and, disposing of said treated aqueous sewage solution, after said filtering.

18. A process for disinfecting a batch of an aqueous sewage solution to be treated, wherein said process comprises:

employing an apparatus that includes:

a first part and a second part;

the first part including a tank for receiving the aqueous sewage solution to be treated;

the second part including piping in fluid communication with said tank;

said piping including an inlet mounted to draw the aqueous sewage solution to be treated from said tank, said piping including an outlet mounted to return the aqueous sewage solution to said tank;

a pump mounted to urge the aqueous sewage solution from said tank, through said second part, and then back into said tank; and a source of ozone operable to introduce ozone into said second part of said apparatus;

establishing the batch of the aqueous sewage solution to be treated in said tank, said batch of aqueous sewage solution having a batch volume;

urging flow of the aqueous sewage solution to be treated through said second part of said apparatus;

establishing a pressure portion of said second part of said apparatus upstream of said outlet, pressure in said pressure portion being an elevated pressure relative to pressure in said tank;

maintaining the pressure in said pressure portion at a pressure of at least 1.5 atm;

said step of urging including raising pressure in said aqueous sewage solution to the pressure of said pressure portion;

dissolving ozone in said aqueous sewage solution;

treating said aqueous sewage solution with said ozone during passage thereof through said pressure portion while under the elevated pressure; and returning said aqueous sewage solution to said tank;

the step of returning including allowing said aqueous sewage solution to return to the pressure of the tank;

repeatedly recirculating said aqueous sewage solution to be treated from said tank through said second part and back to said tank for at least five minutes, until treatment of said batch has been completed; and said recirculating including recirculating a volume of flow corresponding to at least three and one third times said batch volume through said pressure portion during said process.

19. The process of claim 18 wherein said process includes establishing a residence time of said aqueous sewage solution being treated in said pressure portion, said residence time in said pressure portion being at least 2 seconds.

20. The process of claim 19 wherein said residence time is at least 6 seconds.

21. The process of claim 19 wherein said residence time is at least 12 seconds.

22. The process of claim 19 wherein said pressure portion is maintained at a pressure of at least 2 atm.

23. The process of claim 18 wherein said recirculating continues for at least 30 minutes.

24. The process of claim 18 wherein said process includes off-gassing nitrogen from said tank during said process.

25. The process of claim 18 wherein said process additionally includes passing treated aqueous sewage solution through a filter after said treatment is completed to remove phosphorous.

26. The process of claim 18 wherein said process includes returning said aqueous sewage solution from said outlet into said tank at a level above the liquid level in said tank.

27. The process of claim 18 wherein said process includes returning aqueous sewage solution from said outlet into said tank at a level below the liquid level in said tank.

28. The process of claim 18 wherein said process includes maintaining said elevated pressure in said pressure portion of said second part by one of (a) mounting an adjustable valve upstream of said outlet; (b) mounting a restrictor in said second part upstream of said outlet; and (c) using an extra long conduit of pipe mounted within said tank.

29. The process of claim 18 wherein said process includes mounting a restriction within said second part downstream of said pump and upstream of said outlet, and using said restriction in conjunction with said pump to maintain said elevated pressure.

30. The process of claim 29 wherein including using a valve as said restriction.

31. The process of claim 18 wherein said process includes introducing said ozone into said pressure portion.

32. The process of claim 18 wherein the tank has a conical bottom, and the process includes drawing said aqueous sewage solution to be treated into said inlet from said bottom of said tank whereby aqueous fluid to be treated drawn in at said inlet may tend to contain sediment or other material to be treated.

33. The process of claim 18 where an oxidation-reduction potential sensor is located within said second part.

34. The process of claim 33 wherein said process continues until the oxidation reduction potential of the aqueous sewage solution to be treated exceeds +650 mV.

35. The process of claim 34 wherein said process continues until the oxidation reduction potential of the aqueous sewage solution to be treated exceeds +800 mV.

36. The process of claim 18 wherein the pump is selected and operated to pump a flow volume of at least 10 times the batch volume during treatment thereof.

37. The process of claim 18 wherein the pump is selected and operated to pump a quantity of aqueous sewage solution equal to at least 13 times the batch volume.

38. The process of claim 18 wherein the pump is selected and operated so as to pump a flow volume of at least 20 times the batch volume during treatment thereof.

39. The process of claim 18 wherein the pump can be operated to cycle the volume of the tank through said second part at a rate of 20 cycles in 30 minutes.

40. The process of claim 18 wherein said process continues for between 10 and 40 minutes.

* * * * *